US00PP26265P2

(12) United States Plant Patent
Hartman

(10) Patent No.: US PP26,265 P2
(45) Date of Patent: Dec. 22, 2015

(54) ***CALADIUM* PLANT NAMED 'RS-03-03'**

(50) Latin Name: *Caladium×hortulanum*
Varietal Denomination: RS-03-03

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 201 days.

(21) Appl. No.: 13/998,471

(22) Filed: Nov. 4, 2013

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Anne Grunberg
(74) *Attorney, Agent, or Firm* — C. A. Whealy

(57) ABSTRACT

A new and distinct cultivar of *Caladium* plant named 'RS-03-03', characterized by its compact and uniformly mounded plant habit; vigorous growth habit and rapid growth rate; relatively short crop time; lance-type leaves that are pearlescent white to greenish white in color with dark green-colored margins and white to greenish white-colored venation; and good landscape performance.

4 Drawing Sheets

Botanical designation: *Caladium×hortulanum.*
Cultivar denomination: 'RS-03-03'.

BACKGROUND OF THE INVENTION

The present invention relates to a new and distinct cultivar of *Caladium* plant, botanically known as *Caladium×hortulanum*, commercially referred to as a lance (strap) leaf-type *Caladium* and hereinafter referred to by the name 'RS-03-03'.

The objective of the Inventor's breeding program is to create new *Caladium* plants that have uniform plant habit, exceptional container and garden performance and attractive and unique leaf coloration.

The new *Caladium* plant originated from a self-pollination made by the Inventor in April, 2004 in Avon Park, Fla. of *Caladium×hortulanum* 'White Wing', not patented. The new *Caladium* plant was discovered and selected by the Inventor as a single plant within the progeny of the stated self-pollination in a controlled outdoor nursery environment in Zolfo Springs, Fla. on September, 2005.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since April, 2006 has shown that the unique features of this new *Caladium* plant are stable and reproduced true to type in successive generations of asexual reproduction.

SUMMARY OF THE INVENTION

Plants of the new *Caladium* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'RS-03-03'.

These characteristics in combination distinguish 'RS-03-03' as a new and distinct *Caladium* plant:

1. Compact and uniformly mounded plant habit.
2. Vigorous growth habit and rapid growth rate; relatively short crop time.
3. Lance-type leaves that are pearlescent white to greenish white in color with dark green-colored margins and white to greenish white-colored venation.
4. Good landscape performance and relatively tolerant to high light conditions.

Plants of the new *Caladium* differ primarily from plants of the parent, 'White Wing', in the following characteristics:

1. Plants of the new *Caladium* are shorter and more compact than plants of 'White Wing'.
2. Plants of the new *Caladium* grow faster and produce finished plants about one week earlier than plants of 'White Wing'.
3. Plants of the new *Caladium* and 'White Wing' differ in leaf color as leaves of plants of 'White Wing' are creamy white in color with mottled green-colored margins, red-colored petiole junctions and pink-tinged venation.
4. Plants of the *Caladium* and 'White Wing' differ in leaf petiole coloration.

Plants of the new *Caladium* can be compared to plants of *Caladium×hortulanum* 'Mt. Everest', disclosed in U.S. Plant Pat. No. 18,764. In side-by-side comparisons, plants of the new *Caladium* differed primarily from plants of 'Mt. Everest' in the following characteristics:

1. Plants of the new *Caladium* were shorter and more mounded than plants of 'Mt. Everest'.
2. Plants of the new *Caladium* produced finished plants about one to two weeks earlier than plants of 'Mt. Everest'.
3. Plants of the new *Caladium* and 'Mt. Everest' differed in leaf color as leaves of plants of 'Mt. Everest' were creamy white to greyed green in color with dark green-colored margins and reddish pink-colored petiole junctions and venation.

Plants of the new *Caladium* can be compared to plants of *Caladium×hortulanum* 'White Marble', disclosed in U.S. Plant Pat. No. 18,819. In side-by-side comparisons, plants of the new *Caladium* differed primarily from plants of 'White Marble' in the following characteristics:

1. Plants of the new *Caladium* were shorter and more mounded than plants of 'White Marble'.
2. Plants of the new *Caladium* produced finished plants about one to two weeks earlier than plants of 'White Marble'.
3. Plants of the new *Caladium* and 'White Marble' differed in leaf color as leaves of plants of 'White Marble' had creamy white and green-colored Intervenal areas, random white-colored spots often tinged with pink, dark green-colored margins and greenish creamy white-colored venation.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'RS-03-03' in a 15-cm container and grown in a shadehouse.

The photograph at the top of the second sheet is a comparison view of typical plants of 'RS-03-03' grown in 15-cm containers; the plant on the left has not had its tuber de-eyed and the plant on the right has had its tuber de-eyed prior to planting.

The photograph at the bottom of the second sheet is a close-up view of typical freshly-harvested tubers and roots of 'RS-03-03' plants.

The photograph Aar the top of the third sheet is side perspective view of typical plants of 'RS-03-03' grown in an open field.

The photograph at the bottom of the third sheet is a close-up view of developing and fully developed inflorescences of 'RS-03-03'.

The photograph at the top of the fourth sheet is a comparison view of typical potted plants of 'Mt. Everest' (left), 'RS-03-03' (center) and 'White Marble (right).

The photograph at the bottom of the fourth sheet is a comparison view of typical potted plants of the parent, 'White Wing' (left) and 'RS-03-03' (right).

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight in an outdoor nursery in Zolfo Springs, Fla. The plants were grown under cultural practices typical of commercial shadehouse and outdoor nursery production. During the production of the plants, day temperatures ranged from about 29° C. to 33° C. (shadehouse) or 29° C. to 35° C. (outdoor nursery), night temperatures ranged from about 22° C. to 25° C. (shadehouse) or 23° C. to 26° C. (outdoor nursery) and light levels were about 8,000 foot-candles (shadehouse) or 10,000 to 12,000 foot-candles (outdoor nursery). Plants grown in the shadehouse were seven weeks old and plants grown in the outdoor nursery were six months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'RS-03-03'.

Parentage:

*Female, or seed, parent.*—*Caladium×hortulanum* 'White Wing', not patented.

*Male, or pollen, parent.*—*Caladium×hortulanum* 'White Wing', not patented.

Propagation:

*Type.*—By "chipping" the tubers.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented and somewhat flattened; individual segments ovate in shape. Height: About 4.2 cm. Diameter: About 5 cm. Segment height: About 3.2 cm. Segment diameter: About 3 cm. Texture: Thick, starchy; somewhat brittle. Color: Epidermis, freshly-harvested: Close to N170C to N170D and 174B to 174C. Epidermis, dried: Close to 200A to 200B. Cortical tissue: Close to 158B to 158D. Axillary buds: Close to 27D and 155C. Root description: Thick, fleshy contractile roots; color, close to 155C. Rooting habit: Dense.

Plant description:

*Plant type.*—Herbaceous perennial; suitable as a potted plant in containers 15-cm to 25-cm and suitable as a landscape plant in shaded areas.

*Plant and growth habit.*—Compact and uniformly mounded plant habit; vigorous and dense growth habit; rapid growth rate, potted plants in finished or saleable form in about six to seven weeks after planting tubers; leaf petioles and leaves arise from one or more growing points on tubers; petioles mostly upright and leaning outwardly with development.

*Plant height, from soil level to top of foliar plane, shadehouse-grown potted plants.*—About 16 cm to 20 cm.

*Plant height, from soil level to top of inflorescences, shadehouse-grown potted plants.*—About 22 cm.

*Plant diameter or spread, shadehouse-grown potted plants.*—About 25 cm to 29 cm.

*Number of shoots per plant, shadehouse-grown potted plants.*—About 15 shoots develop per #1 tuber.

*Cataphylls, shadehouse-grown potted plants.*—Length: About 5 cm. Width: About 1.3 cm. Shape: Ligulate. Apex: Acute. Base: Sheathing the stem. Color, inner and outer surfaces: Close to 147B to 147C variably streaked and stippled with close to between N186C and N199B; with development, color becoming closer to 199C.

Leaf description:

*Arrangement and type.*—Alternate; simple; lance-type.

*Length, shadehouse-grown potted plants.*—About 12 cm to 15 cm.

*Width, shadehouse-grown potted plants, flattened.*—About 7 cm to 9.5 cm.

*Shape.*—Ovate to lanceolate.

*Apex.*—Acuminate.

*Base*.—Sagittate to sagittate-peltate.

*Margin*.—Entire; mostly flat with broad undulations; fully expanded leaves folded upright along the midrib.

*Texture, upper surface*.—Smooth, glabrous; flexible; dull sheen.

*Texture, lower surface*.—Smooth, glabrous; glaucous.

*Venation pattern*.—Pinnate.

*Color, shadehouse-grown potted plants*.—Developing leaves, upper surface: Main colors: Center, close to 155C; towards the margins, close to 194B to 194C, 147A and 146C to 146D; margins, close to 147A and 146C to 146D. Basal notch: Very faint thin line, close to 187A. Midrib: Close to 157C; distally, close to 157B to 157C. Primary veins: Close to 157A. Developing leaves, lower surface: Main colors: Center, close to 155C; towards the margins, close to 147B to 147C; margins, close to 147C and 191A. Basal notch: Very faint thin line, close to 187A. Midrib: Close to 145D tinged with close to N170D; distally, close to between 193A and 145B. Primary veins: Close to 145B to 145C. Fully expanded leaves, upper surface: Main colors: Center, close to 192C and 194B; towards the margins, close to 146A and 147A; margins, close to 147A to 147B. Basal notch: Very faint thin line, close to 187A. Midrib: Close to 157A tinged with close to 195B; distally, close to 157A. Primary veins: Close to 192C. Fully expanded leaves, lower surface: Main colors: Center, close to 192C to 192D; towards the margins, close to 191A to 191B; margins, close to 191A. Basal notch: Very faint thin line, close to 187A. Midrib: Close to 157B very faintly tinged with close to N170D; distally, close to 145C. Primary veins: Close to 145B.

*Petiole*.—Aspect: Initially upright and straight; with development, leaning outwardly; flexible. Length, shadehouse-grown potted plants: About 14 cm to 16 cm. Diameter, distal, shadehouse-grown potted plants: About 3.4 mm. Diameter, proximal, shadehouse-grown potted plants: About 8 mm. Color, shadehouse-grown potted plants: Just below the leaf and petiole junction: Close to 147C to 147D. Overall: Close to 160D and 147D variably streaked and stippled with close to N199B tinged with close to N186C. Wing length, shadehouse-grown potted plants: About 4.5 cm. Wing diameter, shadehouse-grown potted plants: About 5 mm. Wing color, shadehouse-grown potted plants, inner and outer surfaces: Close to 147B to 147C variably streaked and stippled with close to between N186C and N199B.

Inflorescence description: Inflorescences observed on eight week-old shadehouse-grown potted plants.

*Inflorescence arrangement*.—Upright hooded spathes surrounding a columnar spadix borne on a tall upright scape; spadix with sessile, simple female and male flowers separated into two zones; female flowers develop on the lower one-third of the spadix; male flowers develop on the upper two-thirds of the spadix; sterile flowers develop at junction of female and male flower zones; near this junction, the spathe constricts and surrounds and encloses the female flowers; spathe open and cupped around male flowers.

*Fragrance*.—None detected.

*Natural flowering season and flower longevity*.—Plants of the new *Caladium* typically flower during the spring or early summer in central Florida; flowers develop about four weeks after growth commences; inflorescences last about three days before fading; inflorescences persistent.

*Spathe*.—Length, overall: About 13.6 cm. Length, distal open portion: About 9.6 cm. Length, proximal closed portion: About 4 cm. Width, distal open portion: About 4.6 cm. Width, at constriction: About 1.65 cm. Width, proximal closed portion: About 2.4 cm. Shape: Ovate. Apex: Acuminate. Base: Tapering to the peduncle. Margin: Entire. Texture, front and rear surfaces: Smooth, glabrous. Color, front surface: Distal open portion: Close to between 157B and 145D; with development, color becoming closer to 199C to 199D. Proximal closed portion: Close to 147B to 147C; with development, color becoming faintly mottled with close to 146B to 146C. Color, rear surface: Distal open portion: Close to between 157B and 145B to 145C. Proximal closed portion: Close to 147B to 147C faintly mottled with close to 146B to 146C.

*Spadix*.—Length: About 7.4 cm. Length, male flower zone: About 5.8 cm. Length, sterile zone: About 1.7 cm. Length, female flower zone: About 1.5 cm. Diameter, male flower zone: About 1 cm. Diameter, sterile flower zone: About 7.5 mm. Diameter, female flower zone: About 1 cm. Shape: Columnar, spindle-shaped. Apex: Obtuse. Base: Obtuse. Aspect: Upright. Color, mature, male zone: Close to 158A tinged with close to 150D. Color, mature, sterile zone: Close to 158A tinged with close to 150D. Color, mature, female zone: Close to 20D and 159A. Male flowers: Quantity per spadix: About 140. Shape: Obovate. Height: About 3 mm. Diameter: About 3 mm. Pollen amount: Scarce. Pollen color: Close to 11D. Female flowers: Quantity per spadix: About 160. Shape: Obovate. Height: About 2 mm. Diameter: About 1.2 mm. Stigma color: Close to 20D and 159A. Ovary color: Close to 155D.

*Scape*.—Length: About 18 cm. Diameter: About 7 mm. Strength: Sturdy; flexible. Aspect: Mostly erect. Texture: Smooth, glabrous; glaucous. Color: Between 147B and 146B variably streaked and faintly mottled with close to N186C and N199B.

*Seeds and fruits*.—Seed and fruit development have not been observed on plants of the new *Caladium*.

Disease & pest tolerance: Plants of the new *Caladium* have been observed to have above average tolerance to *Xanthomonas* Leaf Spot and to have average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11.

It is claimed:

1. A new and distinct *Caladium* plant named 'RS-03-03' as illustrated and described.

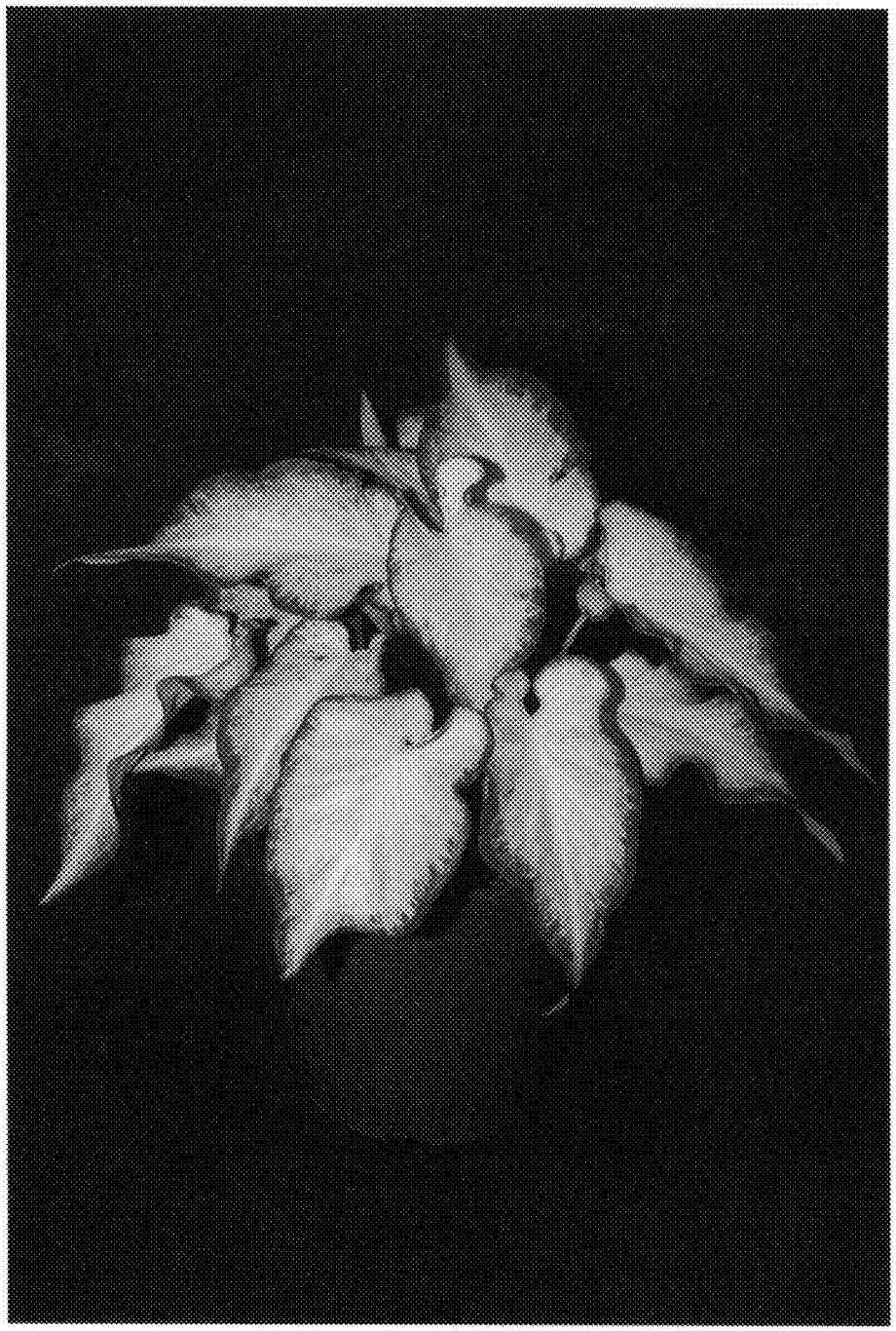

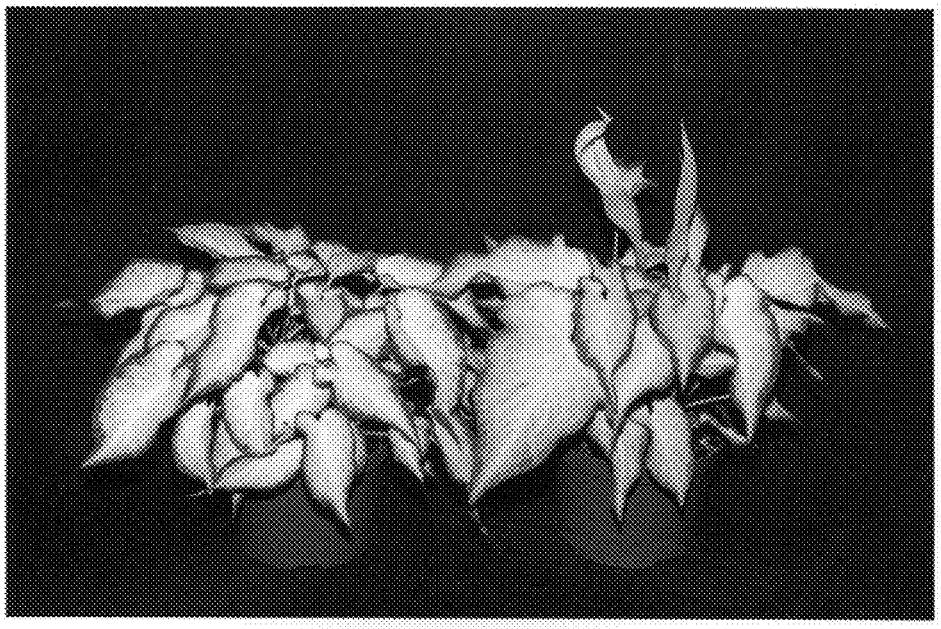
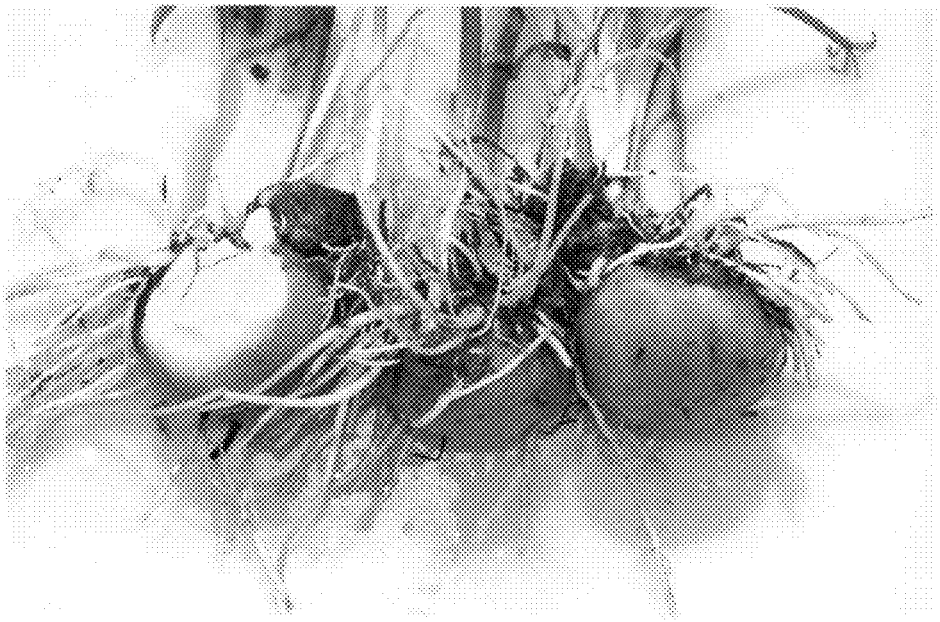

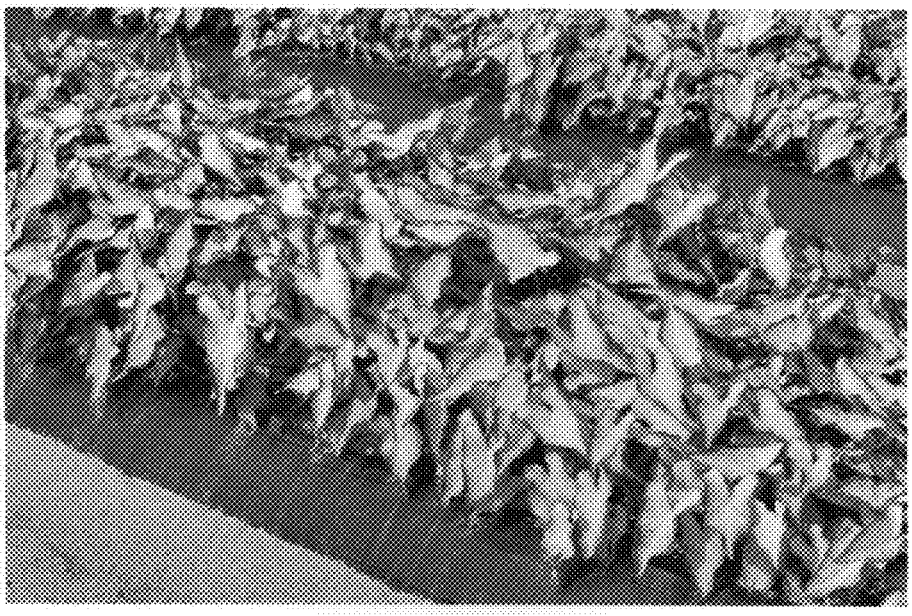
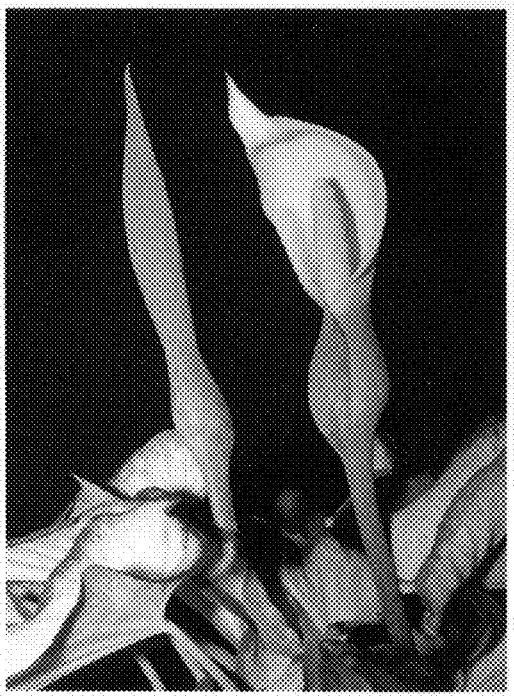

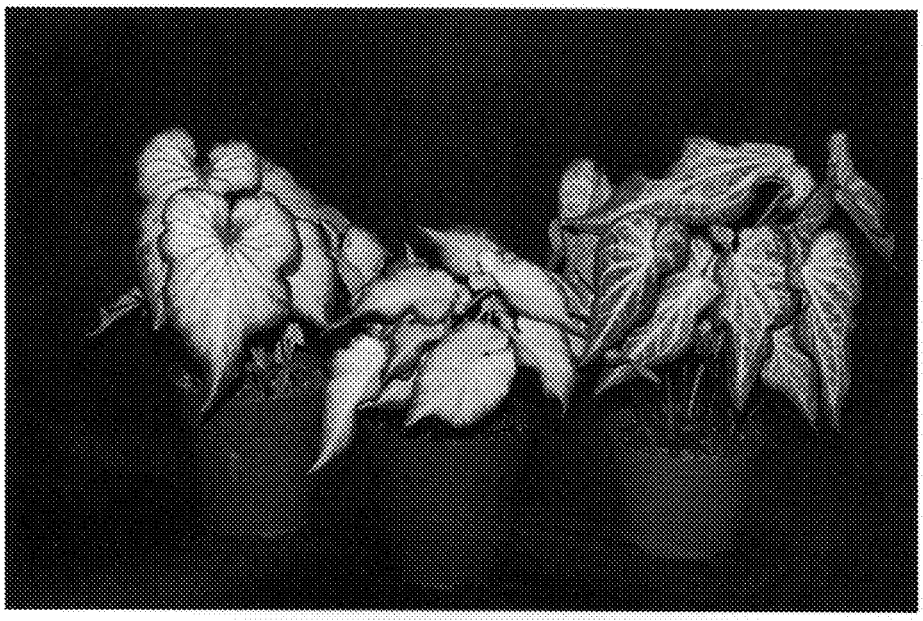
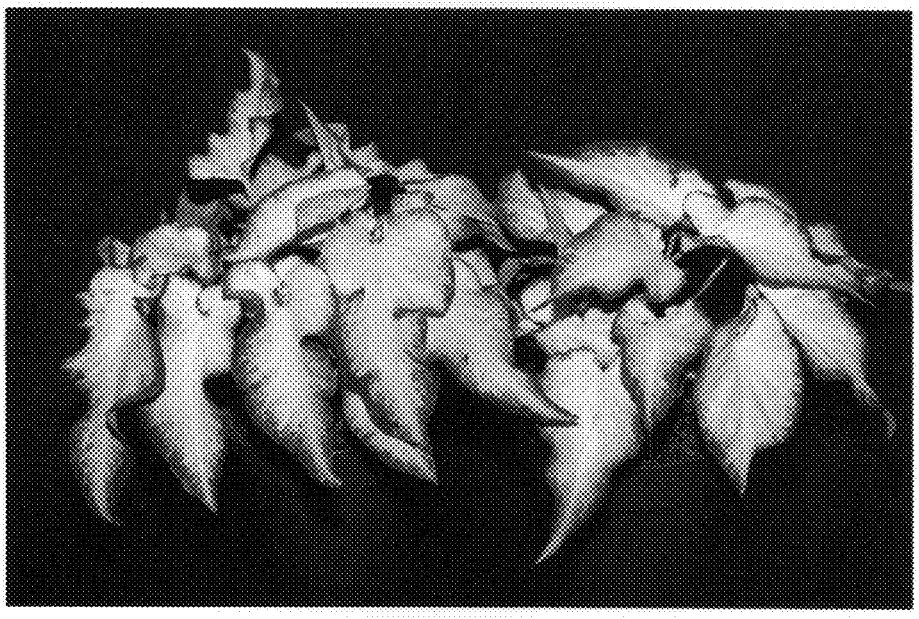

* * * * *